(12) United States Patent
Elevelt et al.

(10) Patent No.: US 11,583,250 B2
(45) Date of Patent: Feb. 21, 2023

(54) ULTRASOUND PROBE POSITIONING SYSTEM AND METHOD OF HANDS-FREE CONTROLLING THE PRESSURE APPLIED BY AN ULTRASOUND PROBE TO AN EXTERNAL OBJECT

(71) Applicant: KONINKLIJKE PHILIPS N.V., Eindhoven (NL)

(72) Inventors: Aaldert Jan Elevelt, Best (NL); Wilhelmus Josephus Box, Eksel (BE); Saskia Maria Camps, Eindhoven (NL); Jacobus Sigbertus Marie Geraats, Eindhoven (NL); Antonius Leonardus Johannes Van Noort, Best (NL); Antonius Maria Rijken, Nuenen (NL); Jacek Lukasz Kustra, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 22 days.

(21) Appl. No.: 17/057,764

(22) PCT Filed: May 28, 2019

(86) PCT No.: PCT/EP2019/063892
§ 371 (c)(1),
(2) Date: Nov. 23, 2020

(87) PCT Pub. No.: WO2019/229099
PCT Pub. Date: Dec. 5, 2019

(65) Prior Publication Data
US 2021/0298719 A1 Sep. 30, 2021

(30) Foreign Application Priority Data

May 28, 2018 (EP) ...................................... 8174487

(51) Int. Cl.
*A61B 8/00* (2006.01)

(52) U.S. Cl.
CPC ............ *A61B 8/4254* (2013.01); *A61B 8/429* (2013.01); *A61B 8/4218* (2013.01)

(58) Field of Classification Search
CPC ...... A61B 8/4254; A61B 8/429; A61B 8/4218
See application file for complete search history.

(56) References Cited

U.S. PATENT DOCUMENTS

| 6,390,982 B1 | 5/2002 | Bova |
| 9,248,316 B2 | 2/2016 | Lachaine |
| (Continued) | | |

FOREIGN PATENT DOCUMENTS

| JP | 2008168063 A | 7/2008 |
| JP | 2017159027 A | 9/2017 |
| (Continued) | | |

OTHER PUBLICATIONS

PCT International Search Report, International application No. PCT/EP2019/063892, dated Jun. 27, 2019.
(Continued)

*Primary Examiner* — Serkan Akar
*Assistant Examiner* — Gabriel Victor Popescu
(74) *Attorney, Agent, or Firm* — Sherry Austin (57) ABSTRACT

An ultrasound probe positioning system (100) comprises a positioning unit (102) for holding an ultrasound probe unit (104) and for moving the ultrasound probe unit and positioning it at a target position and a positioning control unit (106) configured to provide target positioning data indicative of a target position that establishes a mechanical contact of the ultrasound probe unit with an external object (110) and to control the mechanical positioning unit in moving and positioning the ultrasound probe at the target position. The positioning unit comprises a force actuation unit (108) configured to adapt a pressing force amount of a mechanical pressing force exerted on the object in response to a varia-
(Continued)

tion of a counterforce amount so as to maintain a predetermined net pressing force amount exerted by the mechanical pressing force against the counterforce.

13 Claims, 6 Drawing Sheets

(56) References Cited

U.S. PATENT DOCUMENTS

| | | | |
|---|---|---|---|
| 2007/0129634 A1* | 6/2007 | Hickey | A61B 8/4218 600/439 |
| 2009/0088639 A1* | 4/2009 | Maschke | A61B 8/4218 600/443 |
| 2010/0204578 A1 | 8/2010 | Schmidt | |
| 2011/0160589 A1 | 6/2011 | Fu | |
| 2012/0074795 A1* | 3/2012 | Nishikawa | F03G 1/02 310/23 |
| 2012/0083692 A1* | 4/2012 | Stoll | A61B 8/4218 600/437 |
| 2017/0252002 A1 | 9/2017 | Mine | |

FOREIGN PATENT DOCUMENTS

| | | |
|---|---|---|
| WO | WO2015099849 A1 | 7/2015 |
| WO | WO2016202620 A1 | 12/2016 |

OTHER PUBLICATIONS

Lachaine M. et al., "Intrafractional Prostate Motion Management With the Clarity Autoscan System", Medical Physics International Journal, vol. 1, No. 1, pp. 72-80, 2013.

Trivedi A. et al., "Development of 3-Dimensional Transperineal Ultrasound for Image Guided Radiation Therapy of the Prostate: Early Evaluations of Feasibility and Use for Inter- and Intrafractional Prostate Localization", Practical Radiation Oncology, vol. 7, issue 1, Jan. 2017, pp. e27-e33.

O'Shea T. et al., "Review of Ultrasound Image Guidance in External Beam Radiotherapy: Treatment Planning and Inter-Fraction Motion Management", Physics in Medicine & Biology, vol. 60, issue 3, Feb. 2015, pp. R77-R114.

Fargier-Voiron M. et al., "Impact of Probe Pressure Variability on Prostate Localization for Ultrasound-Based Image-Guided Radiotherapy", Radiotherapy and Oncology, Apr. 2014; vol. 111m issue 1, pp. 132-137.

* cited by examiner

ULTRASOUND PROBE POSITIONING SYSTEM AND METHOD OF HANDS-FREE CONTROLLING THE PRESSURE APPLIED BY AN ULTRASOUND PROBE TO AN EXTERNAL OBJECT

CROSS-REFERENCE TO RELATED APPLICATIONS

This patent application claims the priority benefit under 35 U.S.C. § 371 of International Patent Application no. PCT/EP2019/063892, filed May 28, 2019, which claims the benefit of European Patent Application No. EP18174487.1, filed on May 28, 2018. These applications are hereby incorporated by reference herein in their entirety.

FIELD OF THE INVENTION

The present invention is directed to an ultrasound probe positioning system and to a method for controlling an ultrasound probe positioning system.

BACKGROUND OF THE INVENTION

Frequent imaging during the course of radiation treatment (image guided RT, IGRT) can assist in providing a more accurate radiation dose delivery to a target and for less toxicity of delivered radiation to normal tissue. In current clinical practice, such frequent imaging is suitably performed using a cone beam computer tomography (CT) scanner. However, this image modality requires an invasive implantation of fiducial markers, adds an additional radiation dose to the patient and does not allow for intra-fraction motion monitoring.

An alternative involves the use of ultrasound (US) imaging. US imaging is harmless for the patient, relatively cheap, and allows for real-time volumetric organ tracking. Ultrasound imaging is used in combination with medical treatment techniques such as, for instance, external beam radiotherapy (external beam RT) or catheterization procedures.

The publication US 2012/0083692 A1 describes a system for contact pressure control in medical diagnostic ultrasound imaging. According to this publication, the compression of tissue within the patient may be measured using ultrasound scanning. The desired amount of compression in the region of interest for diagnosis may be obtained. It is described that, for example in breast imaging, the desired compression for imaging a portion of the breast is compared to compression measured from ultrasound data. Once the desired tissue compression is achieved, the pressure applied by the transducer is maintained while the diagnosis scan occurs. For example, a robotic arm locks or otherwise maintains the pressure during scanning.

SUMMARY OF THE INVENTION

The inventors have recognized that over the course of a treatment involving a plurality of different treatment fractions at different times, the position and shape of a given region of interest can change, due to a variety of reasons. For example, where the bladder or rectum is the region of interest, a different filling may be given in different treatment fractions. In fact, such changes may not only happen between different treatment fractions (inter-fraction), but also during a single treatment fraction (intra-fraction).

It would be beneficial to improve the image information provided by ultrasound imaging techniques in view of inter-fraction as well as intra-fraction changes in the position and shape of a region of interest to be imaged.

According to a first aspect of the present invention an ultrasound positioning system is presented. The ultrasound probe positioning system comprises a controllably drivable positioning unit for holding an ultrasound probe unit and for moving the ultrasound probe unit and positioning it at a target position. The ultrasound probe positioning system also comprises a positioning control unit configured to provide target positioning data indicative of a target position that establishes a mechanical contact of the ultrasound probe unit with an external object and to control the mechanical positioning unit in moving and positioning the ultrasound probe at the target position. The positioning unit comprises a force actuation unit which is operatively connectable to the ultrasound probe unit and which is configured to exert a mechanical pressing force on the ultrasound probe unit against a counterforce exerted on the ultrasound probe unit by the external object upon establishing the mechanical contact at the target position. The force actuation unit is also configured to adapt a pressing force amount of the mechanical pressing force by increasing or decreasing the pressing force amount in response to a variation of a counterforce amount of the counterforce so as to maintain a predetermined net pressing force amount exerted by the mechanical pressing force against the counterforce. In the case of medical applications, the external object is typically a patient, and the region of interest is an internal region of the body.

In accordance with the first aspect, the force actuator of the positioning unit is configured to maintain a predetermined net pressing force amount exerted by the mechanical pressing force against the counterforce by exerting a mechanical pressing force on the ultrasound probe unit. This mechanical pressing force thus has an amount that may vary and depends on the predetermined net pressing force amount and on the counterforce amount exerted by the external object. For once a mechanical contact has been established between the ultrasound probe and the external object, the external object exerts a counterforce on the ultrasound probe, which may have an amount that is variable with time, depending on a current posture, motion or internal condition of the external object.

The ultrasound positioning system of the first aspect is thus advantageously configured to not only ensure identical positioning, but also identical net pressing force conditions between the ultrasound probe unit and an external object. Information regarding the target position is provided by the positioning control unit in the form of target positioning data. It thus enables a hand-free correct positioning of an ultrasound probe unit in both inter-fraction and intra-fraction ultrasound monitoring in positioning the ultrasound probe unit with a reproducible force at the same target position on the object. This way, probe-force induced displacements of organs in a current fraction or between fractions can be prevented. In addition, maintaining a relative constant pressure on the skin during a treatment fraction, even during limited body motion, prevents the presence of air between the probe and the skin which would decrease image quality.

The ultrasound positioning system thus achieves particularly reliable ultrasound image information by maintaining mechanical contact of the ultrasound probe with the external object of identical net pressing force. Regarding inter-fraction changes of the region of interest, the reproducibility of both position and pressing force of the ultrasound probe with respect to the external object achieves an improved comparability of image information obtained from ultrasound images taken at different fractions of a radiation treatment. Regarding intra-fraction changes of the region of interest, it is thus achieved that motion of the object may occur without losing acoustic coupling between the ultrasound probe unit and the object. In most cases, motion of the object goes along with a change in the counterforce exerted by the external object. Also in these cases, the pressing force amount exerted by the mechanical pressing force against the counterforce exerted by the external object is adapted to maintain a predetermined net pressing force amount.

In the following, different embodiments of the ultrasound positioning system of the first aspect of the present invention will be described.

In one embodiment, the ultrasound probe positioning system further comprises a force sensor unit on a contact surface of the ultrasound probe unit. The force sensor is configured to measure the counterforce amount and provide a counterforce signal indicative of a current amount of the counterforce exerted by the external object. The counterforce signal is, in a particular embodiment, received by a user interface unit configured to display a signal indicative of the current amount of counterforce. In an embodiment, the user interface is configured to output an alarm signal when the counterforce signal indicates that an amount of counterforce is exceeding a predetermined threshold value. Alarm signals may for instance be indicative of handling errors or of an object or patient motion that cannot be handled by the ultrasound probe position system.

In an embodiment of an ultrasound probe positioning system that comprises a force sensor unit, the positioning control unit additionally comprises a force control unit that is configured to receive the counterforce signal, to determine, using the received counterforce signal and the predetermined net pressing force amount, a target pressing force amount to be exerted for achieving or maintaining the predetermined net pressing force amount and to generate and provide a force control signal. In this particular embodiment, the force actuation unit comprises a control input for receiving the force control signal and an active force actuator that is configured to generate and exert the target pressing force amount in response to receiving the force control signal. This embodiment is thus advantageously configured to exert an actively maintained or stabilized force, within a given range, without a need of user interaction. A particular embodiment further includes the user interface unit where feedback regarding the current amount of counterforce is provided to a user or to an external device.

An embodiment of the ultrasound probe positioning system that includes a force sensor unit or a force sensor unit and a force control unit additionally comprises a user interface unit that is configured to receive counterforce signal and to provide a status output signal indicative of the current counterforce amount via the user interface unit.

Another embodiment of the ultrasound probe positioning system of the present invention further comprises an optical tracking system. The optical tracking unit in connected to the positioning control unit and configured to detect a respective landmark position of one or more landmark features and to determine the positioning data indicative of the target position in dependence on the detected landmark positions. A non-limiting example of a landmark feature comprises a marker that is used to locate the target position. The marker can be for instance attached to the external object, or to the object's surrounding at a predetermined position with respect to the target position. A particular embodiment comprises an optical tracking unit configured received radiation emitted or reflected by the marker. By use of the marker, the target position can be found, tracked or both found and tracked by the optical tracking unit. In another embodiment, the optical tracking unit is additionally or alternatively configured to apply known image processing techniques by using anatomic or geometrical properties of the external object to determine the target positioning data.

The optical tracking unit can be used in combination with embodiment in accordance with the first aspect of the present invention.

In an alternative embodiment, the target positioning data is manually input by a user based on an expected target position in a coordinated space. In another embodiment, object-specific target positioning data is additionally or alternatively stored in a data base.

In a further embodiment of the ultrasound probe positioning system, the force actuation unit comprises an electromagnetic actuator for exerting the mechanical pressing force, and configured to maintain the predetermined net pressing force amount in response to the variation of the counterforce.

Alternatively, in another embodiment, the force actuation unit comprises a spring actuator for exerting the mechanical pressing force, the spring actuator maintaining the predetermined net pressing force amount in response to the variation of the counterforce by passively adapting its spring length within a total elastic range of the spring actuator. The spring actuator comprises, in an embodiment, an elastically deformable spring. In an alternative embodiment, the spring actuator comprises a fluid-actuated spring, where fluid relates to either gas or liquid.

Advantageously, in embodiments of the probe positioning system comprising a spring actuator, the positioning control unit is configured to provide the target positioning data so as to let the spring actuator assume a partially compressed state within the total elastic range at the target position. This allows for a compensation of motion of the external object in two opposite directions, namely that of the exerted pressing force and that of the counterforce. Preferably, the total elastic range of the spring actuator comprises an operating range between a first spring length associated with a relaxed spring state and a second spring length associated with a fully compressed spring state, and wherein the partially compressed state corresponds to a compression of the spring actuator by a length amount falling within a middle third of the operating range, when measured with respect to the relaxed spring state.

Preferably, the spring actuator is chosen such that over a length of multiple centimeters, the amount of pressing force exerted stays relatively constant. When the ultrasound probe unit is positioned in contact with the object at the target position, the spring actuator exerts a relatively constant and so reproducible pressing force thereupon. By positioning the ultrasound probe unit in such a way that the spring actuator is initially partially compressed, any limited motion of the patient within a given range and in either the direction of the exerted pressing force or in the direction of the counterforce can be compensated by the spring actuator by either compressing further or decompressing within the elastic range. In another embodiment, which is particularly advantageous to compensate a breath-induced motion of a patient, the operating range has an extension correlated with a displacement expected due to the breath induced motion at the target position. In a particular embodiment, the operating range has an extension of 4 centimeters and the mechanical pressing force amount has a variation of at most 10 percent over the operating range. Other embodiments comprise spring actuators with larger or smaller extension ranges which are advantageously chosen in dependence on the external object.

The ultrasound positioning system of the first aspect of the present invention or any of its embodiments can thus be advantageously used in combination with medical treatment techniques such as, for instance, external beam radiotherapy (external beam RT) or catheterization procedure. In the exemplary case of external beam RT, the ultrasound probe is positioned on a patient so that a target region, which is to be treated, and areas at risk, which should receive as low radiation as possible, are imaged. Inter-fraction differences between corresponding positions or volumes of the target region or areas at risk are evaluated and used to re-calibrate radiation dose delivery of the external beam RT.

According to a second aspect of the present invention, a method for controlling operation of an ultrasound probe positioning system is presented. The method comprises:

providing target positioning data indicative of a target position that establishes a mechanical contact of an ultrasound probe unit with an external object;

controllably moving the ultrasound probe unit and positioning it at the target position;

exerting a mechanical pressing force on the ultrasound probe unit against a counterforce exerted on the ultrasound probe unit by the external object upon establishing the mechanical contact at the target position; and adapting a pressing force amount of the mechanical pressing force by increasing or decreasing the pressing force amount in response to a variation of a counterforce amount of the counterforce so as to maintain a predetermined net pressing force amount exerted by the mechanical pressing force against the counterforce.

The method of the second aspect shares the advantages of the ultrasound probe positioning system and of any of its embodiments.

In an embodiment of the method of the second aspect, the method further comprises detecting a respective landmark position of one or more landmark features and determining the positioning data indicative of the target position in dependence on the detected landmark positions.

Alternatively, or additionally, another embodiment of the method of the second aspect comprises measuring the counterforce amount and providing a counterforce signal indicative of a current amount of the counterforce exerted by the external object.

Yet in another embodiment, adapting a pressing force amount of the mechanical pressing force comprises receiving at a force control unit the counterforce signal, determining, using the received counterforce signal and the predetermined net pressing force amount, a target pressing force amount to be exerted for achieving or maintaining the predetermined net pressing force amount, generating and providing to a force actuation unit a force control signal, and exerting the target pressing force amount in response to receiving the force control signal.

It shall be understood that the ultrasound probe positioning system of claim 1, and the method for controlling operation of an ultrasound probe positioning system of claim 12 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
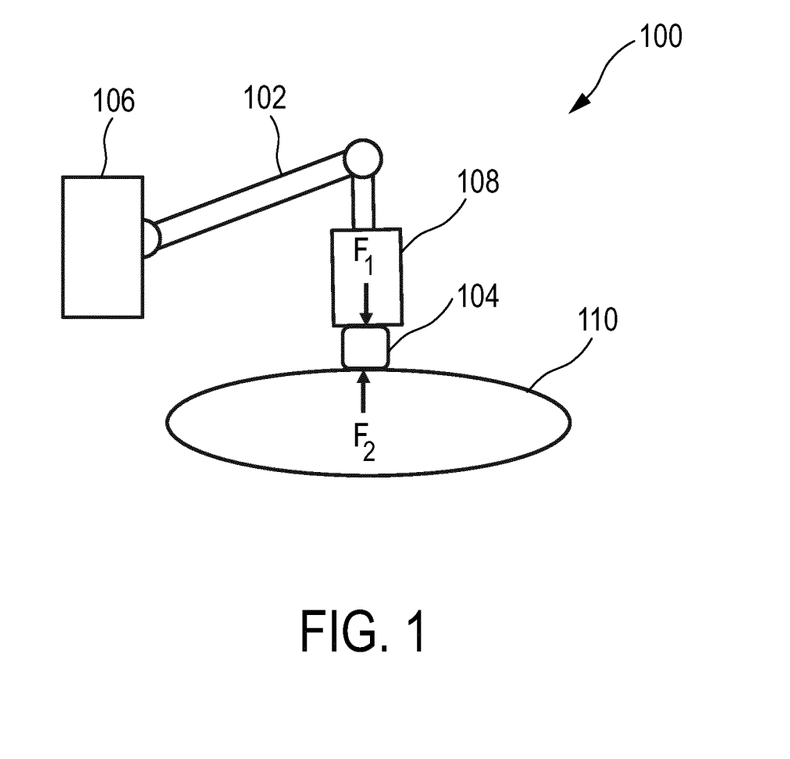
FIG. 1 shows a schematic representation of an embodiment of an ultrasound probe positioning system used on an external object.

FIG. 1 show a schematic block diagram of an embodiment of an ultrasound probe positioning system 100 for positioning an ultrasound probe unit 104 onto an external object 110. The ultrasound probe positioning system 100 comprises a controllably drivable positioning unit 102 for holding the ultrasound probe unit 104 and for moving and positioning it at a target position of the external object 110. In this particular ultrasound probe positioning system, the positioning unit is a mechanical arm. The external object 110 is in this particular case a patient subject of ultrasound monitoring. The ultrasound probe positioning system 100 comprises a positioning control unit 106 configured to provide target positioning data indicative of the target position that establishes a mechanical contact of the ultrasound probe unit 104 with the patient 110 and to control the mechanical positioning unit 102 in moving and positioning the ultrasound probe at the target position.

The positioning unit 102 comprises a force actuation unit 108 that is operatively connectable to the ultrasound probe 104. The force actuation unit is configured to exert a mechanical pressing force ($F_1$) on the ultrasound probe unit against a counterforce ($F_2$) exerted on the ultrasound probe unit by the external object upon establishing the mechanical contact at the target position. The force actuation unit is further configured to adapt a pressing force amount of the mechanical pressing force in response to a variation of a counterforce amount of the counterforce so as to maintain a predetermined net pressing force amount exerted by the mechanical pressing force against the counterforce.

Thus, if the patient 110 moves while being in contact with the ultrasound probe unit and the movement of the patient changes the amount of counterforce exerted on the ultrasound probe unit, the force actuation unit is configured to increase or decrease the exerted pressing force on the ultrasound so that net pressing force amount remains at a relatively constant value. The force actuation unit is advantageously configured to respond to predictable movements that involve a relatively low displacement of the target position such as, but not limited to, breath-induced motion of the patient, heart-beat induced motion of the patient, filling of internal organs of the patient such as bladder or rectum, involuntary movements of small amplitude, hiccup, etc.

The ultrasound probe positioning system 100 achieves improved imaging results also in inter-fraction imaging, for instance in the context of external beam radiotherapy (external beam RT), which is an example of a curative treatment option for cancer. It aims at irradiating tumor a region of interest (ROI), while sparing normal tissue, so called organs at risk (OAR), as much as possible, in order to prevent excessive toxicity that might result in unwanted side-effects. The prescribed radiation dose is typically delivered to the patient in several treatment fractions, which can be spread over several months. By positioning the ultrasound probe at the same position of the body of the patient and setting identical force/pressure of the ultrasound probe on the body in the different fractions, imaging information obtained by the US probe in the different treatment fractions can be better compared and delivers more precise information regarding any changes in the region of interest which need to be taken into account for adapting the location and spatial extension of radiation treatment.

Figure 2:
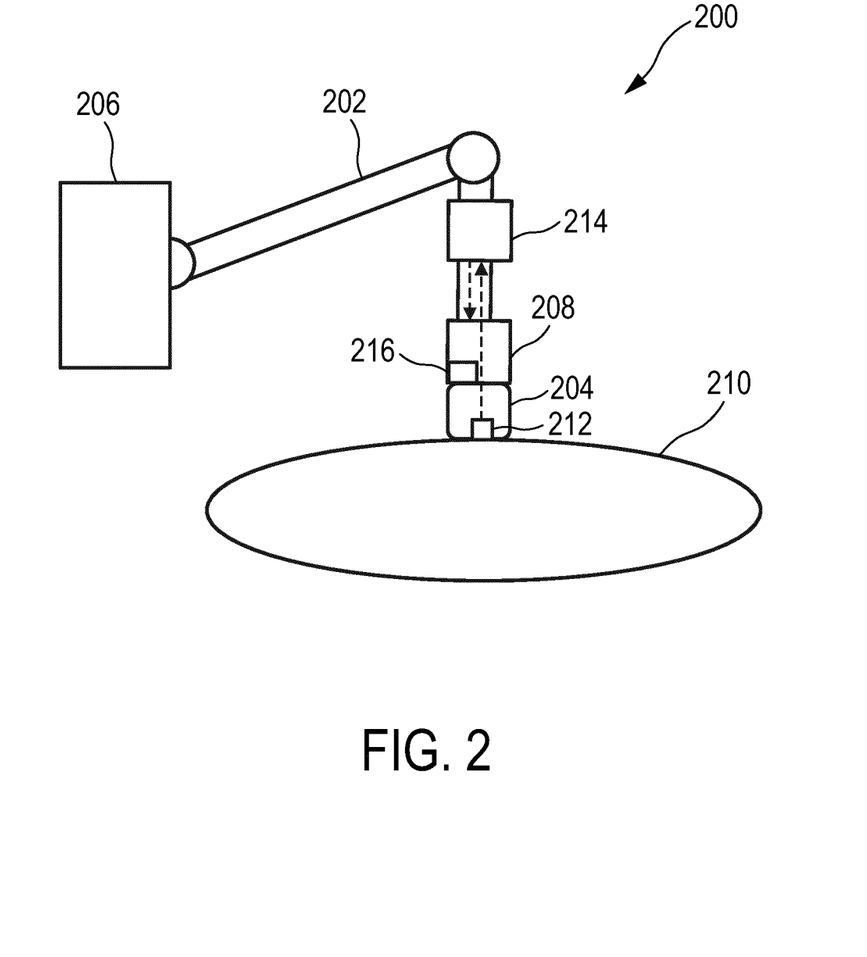
FIG. 2 shows a schematic representation of another embodiment of an ultrasound probe positioning system used on an external object.

FIG. 2 shows a schematic block diagram of another embodiment of an ultrasound probe positioning system 200. The following discussion will focus on the features distinguishing the ultrasound probe positioning system 200 of FIG. 2 from the ultrasound probe positioning system 100 of FIG. 1. Those technical features shared by ultrasound probe positioning systems 100 and 200 are referred to using the same numerals except for the first digit, which is "1" for the ultrasound probe positioning system 100 of FIG. 1 and "2" for the ultrasound probe positioning system 200 of FIG. 2.

The ultrasound probe positioning system 200 comprises a force sensor unit 212. The force sensor unit 212 is arranged on a contact surface of the ultrasound probe unit 204. The force sensor unit 212 is configured to measure the counterforce amount (e.g. $F_2$ in FIG. 1) exerted on the ultrasound probe unit 204 by the patient 210 upon establishing the mechanical contact and to provide a counterforce signal indicative thereof. In the case of the ultrasound probe positioning system 200, the counterforce signal is provided to a force control unit 214, which is configured to determine, using the received counterforce signal and the predetermined net pressing force amount, a target pressing force amount to be exerted for achieving or maintaining the predetermined net pressing force amount. It is also configured to generate a force control signal and to provide it to the force actuation unit 208 via a control input. The force actuation unit 208 comprises an active force actuator 216 configured to generate and exert the target pressing force amount in response to receiving the force control signal.

Figure 3A:
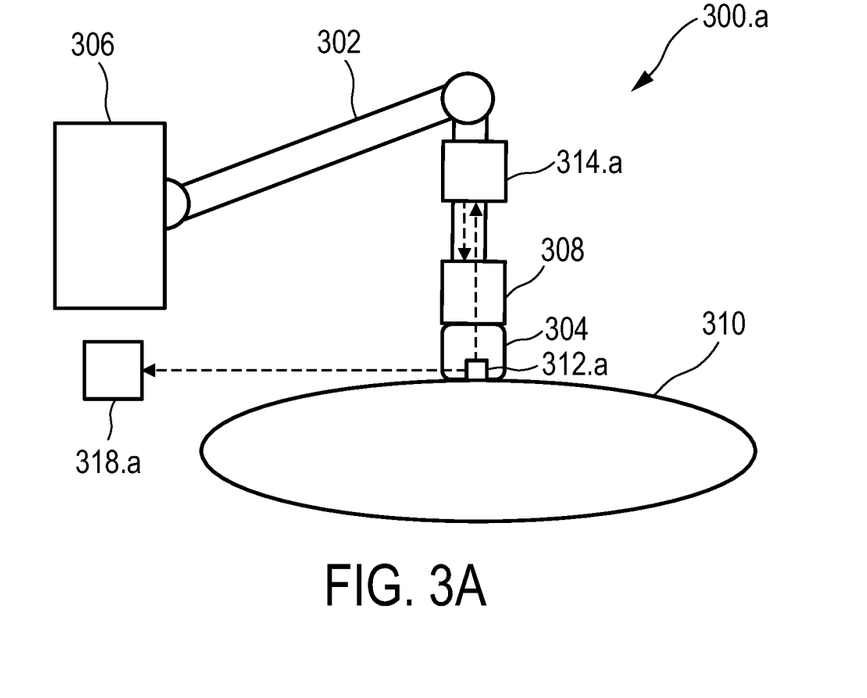
FIG. 3a shows a schematic representation of another embodiment of an ultrasound probe positioning system used on an external object.
Figure 3B:
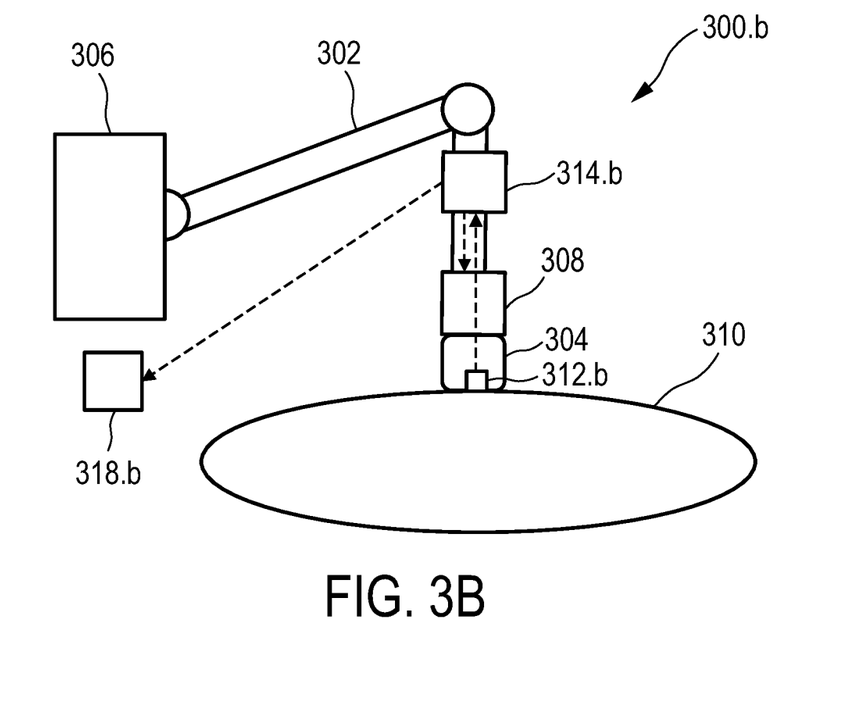
FIG. 3b shows a schematic representation of another embodiment of an ultrasound probe positioning system used on an external object.

FIGS. 3a and 3b show two schematic diagrams of two respective embodiments of an ultrasound probe positioning system 300.a and 300.b. The following discussion will focus on the features distinguishing the ultrasound probe positioning systems 300.a, and 300.b of FIGS. 3a and 3b from the ultrasound probe positioning system 200 of FIG. 2. Those technical features shared by ultrasound probe positioning systems 300.a, 300.b and 200 are referred to using the same numerals except for the first digit, which is "2" for the ultra-sound probe positioning system 200 of FIG. 2 and "3" for the ultrasound probe positioning system 300.a and 300.b of FIGS. 3a and 3b. Features that are different in the ultrasound probe positioning systems 300.a and 300.b are indicated by the presence of the letter "a" or "b" in the numerals.

The ultrasound probe positioning system 300.a comprises a force sensor unit 312.a that is configured to provide the counterforce signal indicative of a current amount of the counterforce exerted by the external object to a user interface unit 318.a. The force sensor unit 312.a also provides the counterforce signal to the force control unit 314.a, as it has been described with reference to FIG. 2. In alternative ultrasound probe positioning systems that do not comprise a force control unit the force sensor unit is configured to provide the counterforce signal solely to the user interface unit.

The ultrasound probe positioning system 300.b comprises a force sensor unit 312.b configured to provide the counterforce signal to the user interface unit 318.b via the force control unit 314.b. Therefore, the force control unit 314.b receives the counterforce signal, determined determines the force control signal based on the counterforce signal and also further provides the counterforce signal received from the force sensor unit 312.b to the user interface unit 318.b.

A particularly advantageous user interface is configured to output an alarm signal when the counterforce signal is indicative that an amount of counterforce is exceeding a predetermined threshold value. Alarm signals may be, for instance, indicative of handling errors or of an object or patient motion that cannot be handled by the ultrasound probe positioning system.

Figure 4:
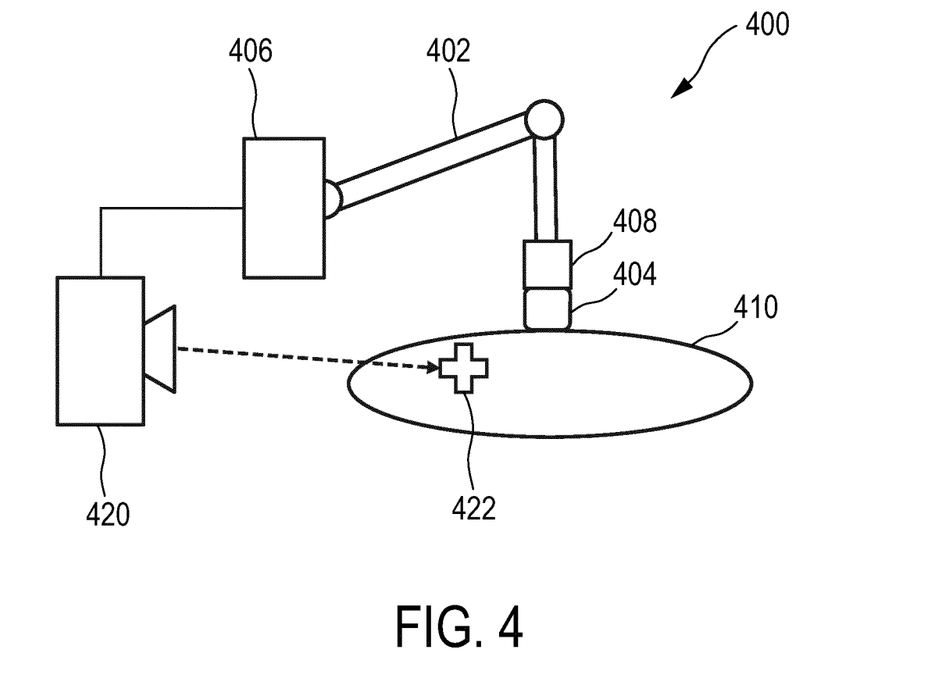
FIG. 4 shows a schematic representation of another embodiment of an ultrasound probe positioning system used on an external object.

FIG. 4 shows a schematic block diagram of another embodiment of an ultrasound probe positioning system 400. The following discussion will focus on the features distinguishing the ultrasound probe positioning system 400 of FIG. 4 from the ultrasound probe positioning system 100 of FIG. 1. Those technical features shared by ultrasound probe positioning systems 100 and 400 are referred to using the same numerals except for the first digit, which is "1" for the ultra-sound probe positioning system 100 of FIG. 1 and "4" for the ultrasound probe positioning system 400 of FIG. 4. The ultrasound probe positioning system 400 comprises an optical tracking unit 420 connected to the positioning control unit 406 and configured to detect a respective landmark position of one or more landmark features 422 and to determine the positioning data indicative of the target position in dependence on the detected landmark positions. The landmark feature 422 is a marker configured to emit or reflect radiation that can be detected by the optical tracking unit 420. The marker can be for instance attached to the external object, or to the object's surrounding at a predetermined position with respect to the target position. By use of the marker 422, the target position can be found, tracked or both found and tracked by the optical tracking unit 420. Alternative optical tracking units are additionally or alternatively configured to apply known image processing techniques by using anatomic or geometrical properties of the external object to determine the target positioning data.

The force actuation unit 108, 208, 308 or 408 may comprise an electromagnetic actuator for exerting the mechanical pressing force, and configured to maintain the predetermined net pressing force amount in response to the variation of the counterforce. Alternatively, the force actuator unit 108, 208, 308 or 408 may comprise a spring actuator for exerting the mechanical pressing force, the spring actuator maintaining the predetermined net pressing force amount in response to the variation of the counterforce by passively adapting its spring length within a total elastic range of the spring actuator. The spring actuator comprises in some force actuation units an elastically deformable spring. In alternative force actuation units, the spring actuator includes a fluid-actuated spring.

Figure 5:
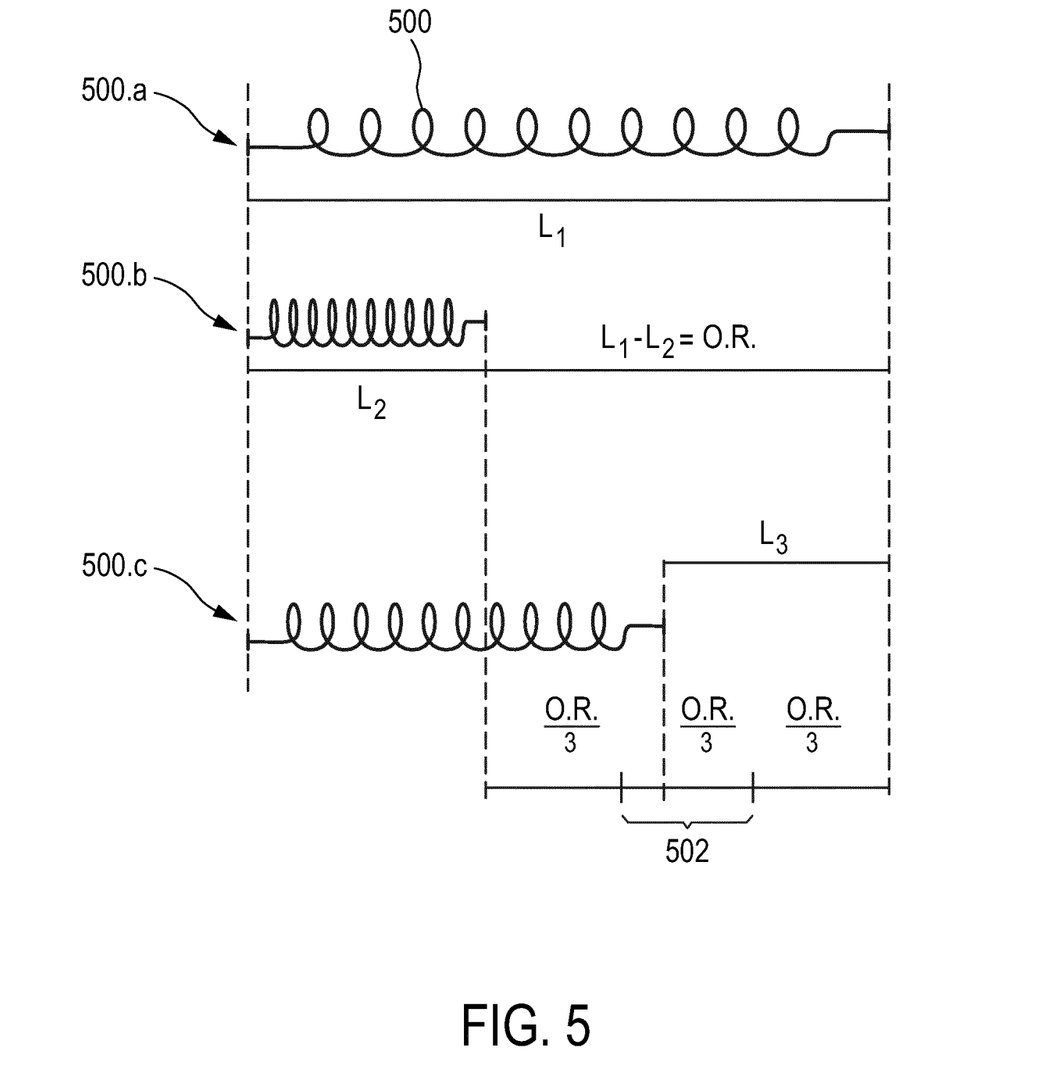
FIG. 5 shows an example of a spring actuator used in a particular embodiment of an ultrasound probe positioning system.

FIG. 5 shows an example of a spring actuator 500 used in a particular embodiment of an ultrasound probe positioning system in three different states. In a first state 500.a, the spring 500 is in a relaxed state and has a first spring length L1. In a second state 500.b, the spring is in a fully compressed state and has a second spring length L2. A maximum operating range OR of the spring is defined by a difference of lengths L1 and L2.

Preferably, the probe positioning unit of an ultrasound probe positioning system comprising spring 500 is configured to provide the target positioning data so as to let the spring actuator assume a partially compressed state 500.c within a total elastic range at the target position, and more preferably, within the operating range. Even more preferably, the partially compressed state corresponds to a compression of the spring actuator by a length amount L3 falling within a middle third 502 of the operating range.

In a particular ultrasound probe positioning system, the operating range of the spring actuator has an extension of at least 4 cm and the mechanical pressing force amount has a variation of at most 10 percent over the operating range. Other spring actuators have larger extensions of the operating range. The choice of the extension depends on a type and amplitude of an expected movement of the patient that would cause a change in the counterforce.

Figure 6:
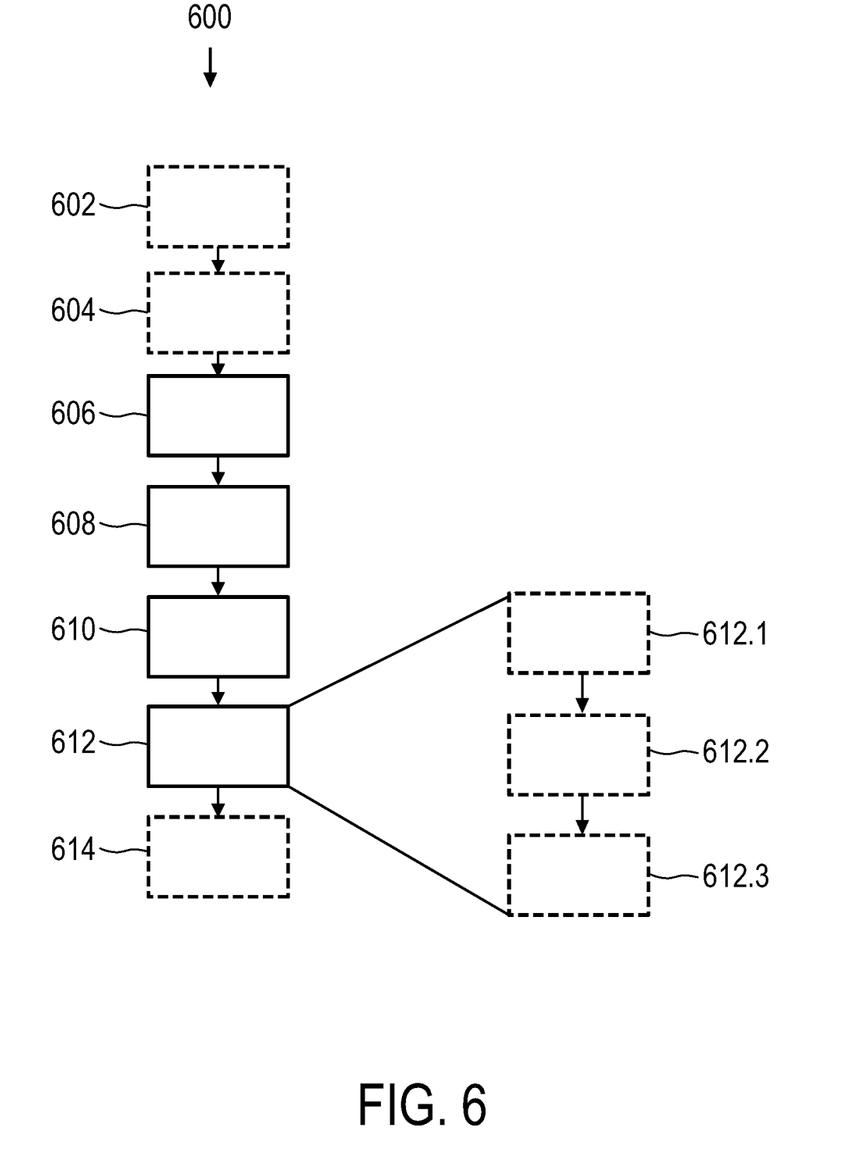
FIG. 6 shows a flow diagram of an embodiment of a method for operating an ultrasound probe positioning system.

FIG. 6 shows a block diagram of an embodiment of a method 600 for controlling operation of an ultrasound probe positioning system. The method includes a step 606 in which target positioning data is provided, the target positioning data being indicative of a target position that establishes a mechanical contact of an ultrasound probe unit with an external object. In a step 608, the method includes controllably moving the ultrasound probe unit and positioning it at the target position. Further, in a step 610, a mechanical pressing force is exerted on the ultrasound probe unit against a counterforce exerted on the ultrasound probe unit by the external object upon establishing the mechanical contact at the target position. Finally, in a step 612, a pressing force amount of the mechanical pressing force is adapted in response to a variation of a counterforce amount of the counterforce so as to maintain a predetermined net pressing force amount exerted by the mechanical pressing force against the counterforce.

Method 600 may also include a step 602, during which a landmark position is detected and another step 604 in which the positioning data indicative of the target position is determined in dependence on the detected landmark positions.

Method 600 may additionally comprise a step 614 in which the counterforce amount is measured and a counterforce signal indicative of a current amount of the counterforce exerted by the external object is provided.

Step 612 of method 600, which involves adapting a pressing force amount of the mechanical pressing force, comprises, in an embodiment, a step 612.1 in which the counterforce signal is received at a force control unit, a step 612.2 in which, using the received counterforce signal and the predetermined net pressing force amount, a target pressing force amount to be exerted for achieving or maintaining the predetermined net pressing force amount is determined and a step 612.3 in which a force control signal is generated and provided to a force actuation unit, and wherein the target pressing force amount is exerted in response to receiving the force control signal.

In summary, an ultrasound probe positioning system is presented that comprises a positioning unit for holding an ultrasound probe unit and for moving the ultrasound probe unit and positioning it at a target position and a positioning control unit configured to provide target positioning data indicative of a target position that establishes a mechanical contact of the ultrasound probe unit with an external object and to control the mechanical positioning unit in moving and positioning the ultrasound probe at the target position. The positioning unit comprises a force actuation unit configured to adapt a pressing force amount of a mechanical pressing force exerted on the object in response to a variation of a counterforce amount so as to maintain a predetermined net pressing force amount exerted by the mechanical pressing force against the counterforce.

In the claims, the word "comprising" does not exclude other elements or steps, and the indefinite article "a" or "an" does not exclude a plurality.

A single step or other units may fulfill the functions of several items recited in the claims. The mere fact that certain measures are recited in mutually different dependent claims does not indicate that a combination of these measures cannot be used to advantage. Any reference signs in the claims should not be construed as limiting the scope.

A net force is defined as the vector sum of individual forces acting on an object. The term net pressing force is used in the context of the present application to convey that the sum of individual forces acting on the ultrasound probe unit results in a net force applying constant pressure on the external object, to which a mechanical contact is to be established and maintained by the ultrasound probe unit during operation of the ultrasound probe positioning system.

The invention claimed is:
1. An ultrasound probe positioning system, comprising:
a controllably drivable positioning unit for holding an ultrasound probe unit and for moving and positioning the ultrasound probe unit at a target position; and
a positioning control unit configured to provide target positioning data indicative of the target position that establishes a mechanical contact of the ultrasound probe unit with an external object and to control the mechanical positioning unit in moving and positioning the ultrasound probe at the target position; wherein
the positioning unit comprises a force actuation unit which is operatively connectable to the ultrasound probe unit and which is configured to exert a mechanical pressing force on the ultrasound probe unit against a counterforce exerted on the ultrasound probe unit by the external object upon establishing the mechanical contact at the target position, and to adapt a pressing force amount of the mechanical pressing force by increasing or decreasing the pressing force amount in response to a variation of a counterforce amount of the counterforce so as to result in a net force of a predetermined net force amount applying a constant pressure on the external object, to which the mechanical contact is to be established and maintained by the ultrasound probe unit during operation of the ultrasound probe positioning system, wherein the positioning control unit further comprises a force control unit that is configured:
to receive the counterforce signal;
to determine, using the received counterforce signal and the predetermined net force amount, a target pressing force amount to be exerted for achieving or maintaining the predetermined net pressing force amount; and to generate and provide a force control signal indicative of the target pressing force; and wherein the force actuation unit comprises a control input for receiving the force control signal and an active force actuator that is configured to generate and exert the target pressing force amount in response to receiving the force control signal.

2. The ultrasound probe positioning system of claim 1, further comprising a force sensor unit on a contact surface of the ultrasound probe unit, which is configured to measure the counterforce amount and provide a counterforce signal indicative of a current amount of the counterforce exerted by the external object.

3. The ultrasound probe positioning system of claim 2, further comprising a user interface unit that is configured to receive the counterforce signal and to provide a status output signal indicative of the current counterforce amount via the user interface unit.

4. The ultrasound probe positioning system of claim 1, further comprising an optical tracking unit connected to the positioning control unit and configured to detect a respective landmark position of one or more landmark features and to determine the positioning data indicative of the target position in dependence on the detected landmark positions.

5. The ultrasound probe positioning system of claim 1, wherein the force actuation unit comprises an electromagnetic actuator for exerting the mechanical pressing force, and configured to maintain the predetermined net force amount in response to the variation of the counterforce.

6. The ultrasound probe positioning system of claim 1, wherein the force actuation unit comprises a spring actuator for exerting the mechanical pressing force, the spring actuator maintaining the predetermined net force amount in response to the variation of the counterforce by passively adapting its spring length within a total elastic range of the spring actuator.

7. The ultrasound probe positioning system of claim 6, wherein the spring actuator comprises an elastically deformable spring or a fluid-actuated spring.

8. The ultrasound probe positioning system of claim 6, wherein the positioning control unit is configured to provide the target positioning data so as to let the spring actuator assume a partially compressed state within the total elastic range at the target position.

9. The ultrasound probe positioning system of claim 8, wherein the total elastic range of the spring actuator comprises an operating range between a first spring length associated with a relaxed spring state and a second spring length associated with a fully compressed spring state, and wherein the partially compressed state corresponds to a compression of the spring actuator by a length amount falling within a middle third of the operating range, when measured with respect to the relaxed spring state.

10. The ultrasound probe positioning system of claim 9, wherein the operating range has an extension of at least 4 cm, and wherein the mechanical pressing force amount has a variation of at most 10 percent over the operating range.

11. A method for controlling operation of an ultrasound probe positioning system, the method comprising:

providing, by a positioning control unit, target positioning data indicative of a target position that establishes a mechanical contact of an ultrasound probe unit with an external object;

controllably moving and positioning the ultrasound probe unit at the target position;

exerting a mechanical pressing force on the ultrasound probe unit against a counterforce exerted on the ultrasound probe unit by the external object upon establishing the mechanical contact at the target position; and adapting a pressing force amount of the mechanical pressing force by increasing or decreasing the pressing force amount in response to a variation of a counterforce amount of the counterforce so as to result in a net force of a predetermined net force amount applying a constant pressure on the external object, to which the mechanical contact is established and to be maintained by the ultrasound probe unit during operation of the ultrasound probe positioning system, wherein adapting a pressing force amount of the mechanical pressing force in response to a variation of a counterforce amount of the counterforce so as to maintain the predetermined net force amount comprises:

receiving, at a force control unit, the counterforce signal;

determining, using the received counterforce signal and the predetermined net force amount, a target pressing force amount to be exerted for achieving or maintaining the predetermined net force amount;

generating and providing to a force actuation unit a force control signal; and exerting the target pressing force amount in response to receiving the force control signal.

12. The method of claim 11 further comprising:

detecting a landmark position; and determining target positioning data indicative of the target position in dependence on the detected land-mark positions.

13. The method of claim 11, further comprising measuring the counterforce amount and providing a counterforce signal indicative of a current amount of the counterforce exerted by the external object.

* * * * *